(12) United States Patent
Takamura et al.

(10) Patent No.: US 11,491,063 B2
(45) Date of Patent: Nov. 8, 2022

(54) BED SYSTEM AND SEPARATION METHOD

(71) Applicant: CANON MEDICAL SYSTEMS CORPORATION, Otawara (JP)

(72) Inventors: Satoshi Takamura, Nasushiobara (JP); Yoichi Hiyama, Sakura (JP); Shigeru Usuda, Otawara (JP); Yurina Otsuka, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 286 days.

(21) Appl. No.: 16/275,717

(22) Filed: Feb. 14, 2019

(65) Prior Publication Data
US 2019/0247253 A1    Aug. 15, 2019

(30) Foreign Application Priority Data

Feb. 15, 2018 (JP) .............................. JP2018-025358

(51) Int. Cl.
*A61G 7/05* (2006.01)
*A61B 5/055* (2006.01)
*G01R 33/28* (2006.01)

(52) U.S. Cl.
CPC ............ *A61G 7/0528* (2016.11); *A61B 5/055* (2013.01); *G01R 33/288* (2013.01); *A61G 2203/22* (2013.01); *A61G 2210/50* (2013.01)

(58) Field of Classification Search
CPC .............. A61G 7/0528; A61G 2203/22; A61G 2210/50; A61G 13/0018; A61B 5/704
See application file for complete search history.

(56) References Cited

U.S. PATENT DOCUMENTS

| 4,671,728 A * | 6/1987 | Clark ................... A61B 6/0487 |
|---|---|---|
| | | 414/401 |
| 2005/0020906 A1* | 1/2005 | Seijger ................... A61B 5/055 |
| | | 600/415 |
| 2005/0034237 A1* | 2/2005 | Lenting .................. A61B 5/055 |
| | | 5/600 |

(Continued)

FOREIGN PATENT DOCUMENTS

| JP | 11-33010 A | 2/1999 |
|---|---|---|
| JP | 2004-267801 A | 9/2004 |
| JP | 2013106676 A * | 6/2013 |

(Continued)

OTHER PUBLICATIONS

Office Action dated Dec. 7, 2021 in Japanese Application No. 2018-025358.

(Continued)

*Primary Examiner* — Eric J Kurilla
(74) *Attorney, Agent, or Firm* — Oblon, McClelland, Maier & Neustadt, L.L.P.

(57) ABSTRACT

According to one embodiment, a bed system that is mechanically and electrically connectable to a main body of a medical image diagnosis apparatus includes a traveling unit and an interface. The traveling unit provided between the bed system and a floor surface. The interface configured to receive an operation of locking or unlocking driving of the traveling unit. The operation on the interface of locking or unlocking driving of the traveling unit is interlocked with electrical connection between the bed system and the main body.

9 Claims, 11 Drawing Sheets

(56) References Cited

U.S. PATENT DOCUMENTS

2009/0158524 A1     6/2009   Patterson et al.
2014/0303477 A1* 10/2014   Sunazuka .............. A61B 5/055
                                                                           600/407

FOREIGN PATENT DOCUMENTS

| JP | 6002678 B2 | 10/2016 |
| JP | 2017-086416 | 5/2017 |
| WO | WO 2013/073552 A1 | 5/2013 |

OTHER PUBLICATIONS

Japanese Office Action dated Jun. 21, 2022 in Japanese Patent Application No. 2018-025358, 3 pages.

* cited by examiner

BED SYSTEM AND SEPARATION METHOD

CROSS-REFERENCE TO RELATED APPLICATIONS

This application claims the benefit of priority of Japanese Patent Application No. 2018-025358, filed Feb. 15, 2018, the entire contents of which are incorporated herein by reference.

FIELD

Embodiments described herein relate generally to a bed system and a separation method.

BACKGROUND

In general, an MRI (Magnetic Resonance Imaging) apparatus includes a bed system for placing patient thereon and a main body installed in an examination room. Among bed systems used for an MRI apparatus, there is known a movable-type bed system which can be moved from a patient room to the examination room with a patient placed thereon and be mechanically and electrically connected to the main body of the MRI apparatus in the examination room.

However, when the bed system and the main body of the MRI apparatus are connected and energized and both are suddenly separated in this connected and energized state due to, e.g., an erroneous operation by a user, there is a risk of damaging the electrical system of the bed system and/or the main body.

DETAILED DESCRIPTION

Figure 1:
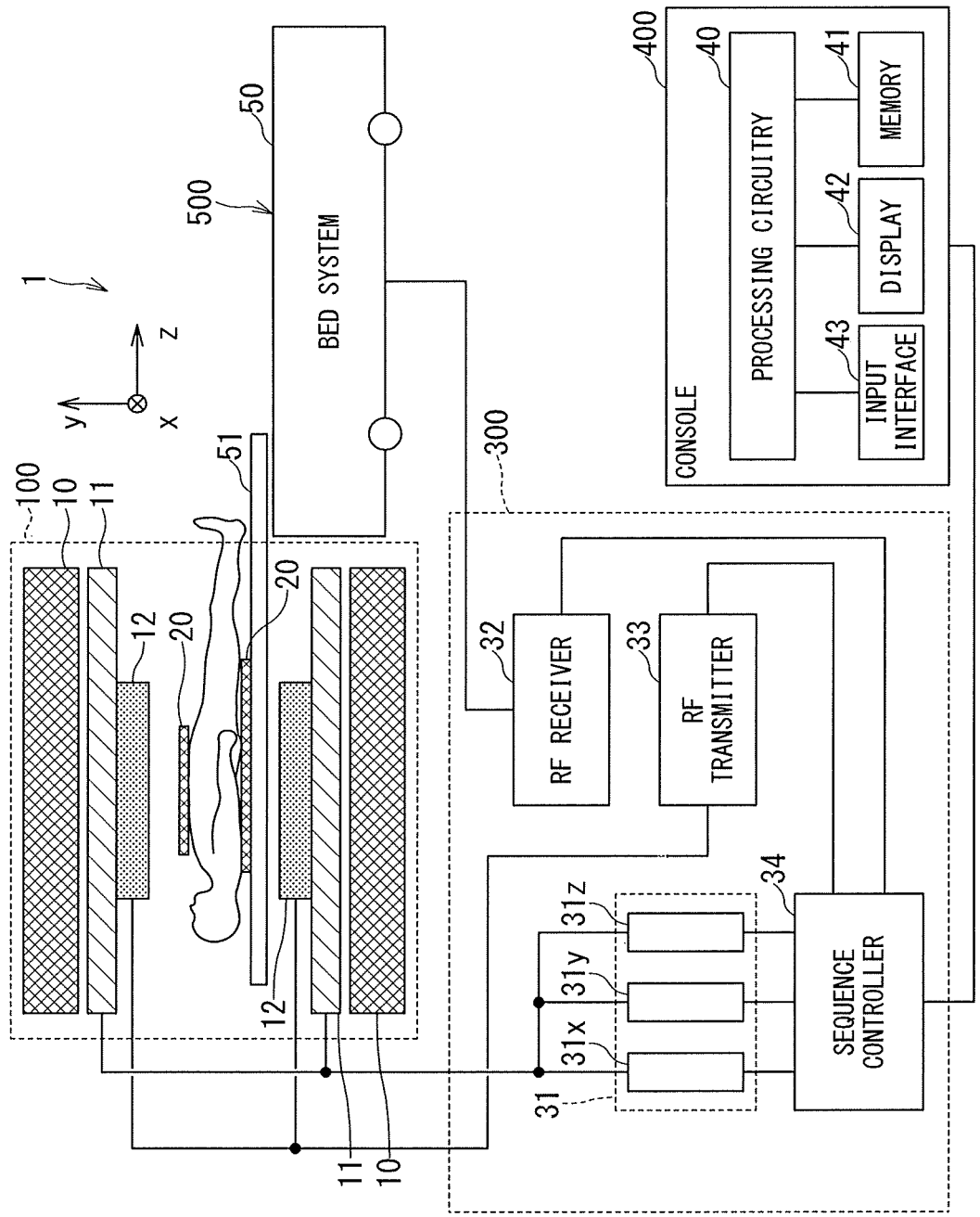
FIG. 1 is a block diagram illustrating a configuration of an MRI apparatus equipped with a bed system according to one embodiment.

Hereinbelow, a description will be given of embodiments of a bed system and a mechanical separation method between the bed system and a main body of an apparatus by referring to the drawings. The bed system according to the embodiment is mechanically and electrically connected to a main body of various modalities (i.e., medical image diagnostic apparatus) which includes, e.g., an X-ray CT apparatus and a nuclear medical diagnostic apparatus such as an MRI apparatus, a SPECT apparatus, and a PET apparatus.

In the following description, a "main body" of a medical image diagnostic apparatus is a unit installed in an imaging room. For instance, in the case of an MRI apparatus, its main body is the unit that accommodates respective components of the imaging system including, e.g., a static magnetic field magnet and a gradient coil. In the case of an X-ray CT apparatus, its main body is the unit that accommodates respective components of the imaging system including, e.g., an X-ray source and an X-ray detector.

In general, according to one embodiment, a bed system that is mechanically and electrically connectable to a main body of a medical image diagnosis apparatus includes a traveling unit and an interface. The traveling unit provided between the bed system and a floor surface. The interface configured to receive an operation of locking or unlocking driving of the traveling unit. The operation on the interface of locking or unlocking driving of the traveling unit is interlocked with electrical connection between the bed system and the main body.

In the following, a description will be given of a case where an MRI apparatus is used as the above-described medical image diagnostic apparatus, the main body of which is mechanically and electrically connected to the bed system according to the embodiment.

FIG. 1 is a block diagram illustrating a configuration of an MRI apparatus 1 including a bed system 500 according to one embodiment. The MRI apparatus 1 includes a main body (also referred to as a gantry) 100, a control cabinet 300, a console 400, the bed system 500, and local RF (Radio Frequency) coils 20. The main body 100, the control cabinet 300, and the bed system 500 are generally installed in an examination room. The console 400 is generally installed in a control room adjacent to the examination room.

The main body 100 includes a static magnetic field magnet 10, a gradient coil 11, and a WB (whole body) coil 12, and these components are housed in a cylindrical housing. The bed system 500 includes a bed body 50 and a table 51. Details of the configuration of bed system 500 will be described below by referring to FIG. 2 to FIG. 10.

The control cabinet 300 includes three gradient coil power supplies 31 (31x for an X-axis, 31y for a Y-axis, and 31z for a Z-axis), an RF receiver 32, an RF transmitter 33, and a sequence controller 34.

The console 400 includes processing circuitry 40, a memory 41, a display 42, and an input interface 43. The console 400 functions as a host computer.

The static magnetic field magnet 10 of the main body 100 is substantially in the form of a cylinder, and generates a static magnetic field inside a bore into which an object, e.g., a patient is transported. The bore is a space inside the cylindrical structure of the main body 100. The static magnetic field magnet 10 includes, e.g., a superconducting coil inside, and the superconducting coil is cooled down to a cryogenic temperature by liquid helium. The static magnetic field magnet 10 generates a static magnetic field by supplying the superconducting coil with an electric current provided from a non-illustrated static magnetic field power supply in an excitation mode. Afterward, the static magnetic field magnet 10 shifts to a permanent current mode, and the static magnetic field power supply is separated. Once it enters the permanent current mode, the static magnetic field magnet 10 continues to generate a static magnetic field for a long time, e.g., over one year. Note that the static magnetic field magnet 10 is not limited to a superconducting magnet equipped with a superconducting coil inside but may be a permanent magnet.

The gradient coil 11 is also substantially in the form of a cylinder and is fixed to the inside of the static magnetic field magnet 10. The gradient coil 11 forms gradient magnetic fields in the respective directions of the X-axis, the Y-axis, and the Z-axis by using electric currents supplied from the gradient coil power supplies 31x, 31y, and 31z.

The bed body 50 of the bed system 500 can move the table 51 in the vertical direction and in the horizontal direction. For instance, the bed body 50 moves the table 51 with an object loaded thereon to a predetermined height before imaging. Afterward, when the object is imaged, the bed body 50 moves the table 51 in the horizontal direction so as to move the object to the inside of the bore.

The WB body coil 12 is shaped substantially in the form of a cylinder so as to surround the object, and is fixed to the inside of the gradient coil 11. The WB coil 12 applies RF pulses transmitted from the RF transmitter 33 to the object. Further, the WB coil 12 receives magnetic resonance signals, i.e., MR signals emitted from the object due to excitation of hydrogen nuclei.

The MRI apparatus 1 includes the local RF coils 20 as shown in FIG. 1 in addition to the WB coil 12. Each of the local RF coils 20 is a coil placed close to the body surface of the object. There are various types for the local RF coils 20. For instance, as the types of the local RF coils 20, as shown in FIG. 1, there are a body coil attached to the chest, abdomen, or legs of the object and a spine coil attached to the back side of the object. The local RF coils 20 may be of a type dedicated for receiving MR signals, another type dedicated for transmitting RF pulses, or another type for performing both of receiving MR signals and transmitting RF pulses. The local RF coils 20 are configured to be attachable to and detachable from the table 51 via a cable, for instance.

The RF receiver 32 performs A/D (Analog to Digital) conversion on the channel signal from the WB coil 12 and/or the local RF coils 20, i.e., the MR signals, and outputs the converted MR signals to the sequence controller 34. The MR signals converted to digital signals are sometimes referred to as raw data.

The RF transmitter 33 generates an RF pulse on the basis of an instruction from the sequence controller 34. The generated RF pulse is transmitted to the WB coil 12 and applied to the object. An MR signal is generated from the object by the application of the RF pulse. This MR signal is received by the local RF coils 20 or the WB coil 12.

The MR signals received by the local RF coils 20, more specifically, the MR signals received by each of the coil elements in the RF coils 20, are inputted to the RF receiver 32 via cables provided on the table 51 and the bed body 50. The sequence controller 34 performs a scan of the object by driving each of the gradient coil power supplies 31, the RF transmitter 33, and the RF receiver 32 under the control of the console 400. When the sequence controller 34 receives raw data from the RF receiver 32 by performing a scan, the sequence controller 34 transmits the received raw data to the console 400.

The sequence controller 34 includes non-illustrated processing circuitry. This processing circuitry is configured as, e.g., a processor for executing predetermined programs or configured as hardware such as an FPGA (field programmable gate array) and an ASIC (application specific integrated circuit).

The console 400 includes a memory 41, a display 42, an input interface 43, and processing circuitry 40.

The memory 41 is a recording medium including a ROM (Read Only memory) and a RAM (Random Access Memory) in addition to an external memory device such as a HDD (Hard Disk Drive) and an optical disc device. The memory 41 stores various programs executed by a processor of the processing circuitry 40 as well as various types of data and information.

The display 42 is a display device such as a liquid crystal display panel, a plasma display panel, and an organic EL panel. The input interface 43 includes various devices for an operator to input various types of information and data, and is configured of, e.g., a mouse, a keyboard, a trackball, and/or a touch panel.

The processing circuitry 40 is, e.g., a circuit equipped with a CPU (Central Processing Unit) and/or a special-purpose or general-purpose processor. The processor implements various functions by executing the programs stored in the memory 41. The processing circuitry 40 may be configured of hardware such as an FPGA and an ASIC. The various functions described below can also be implemented by such hardware. Additionally, the processing circuitry 40 can implement the various functions by combining hardware processing and software processing based on its processor and programs.

Figure 2A:
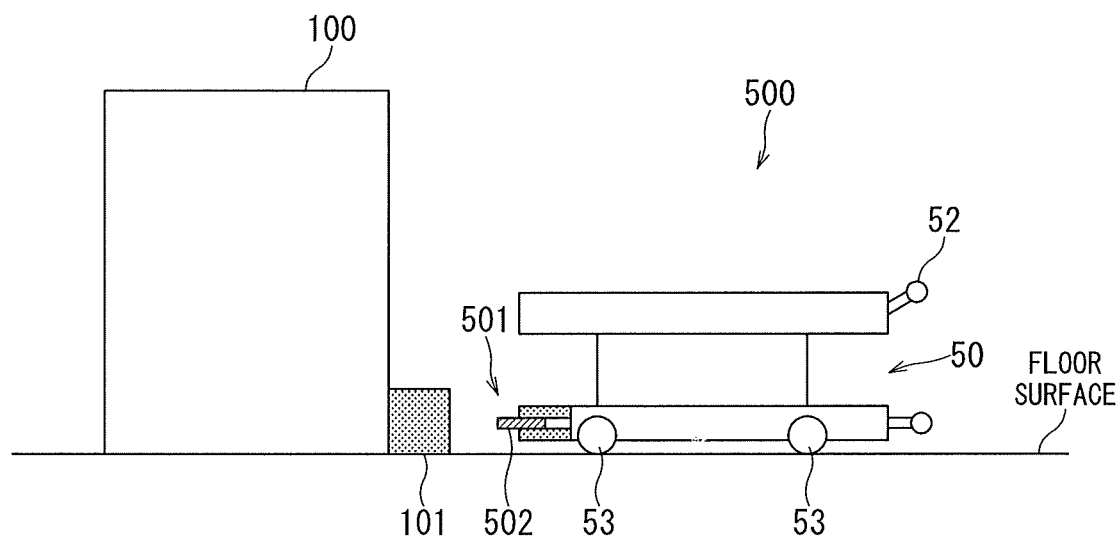
FIG. 2A is a schematic diagram illustrating a state where the bed system is mechanically separated from the main body.
Figure 2B:
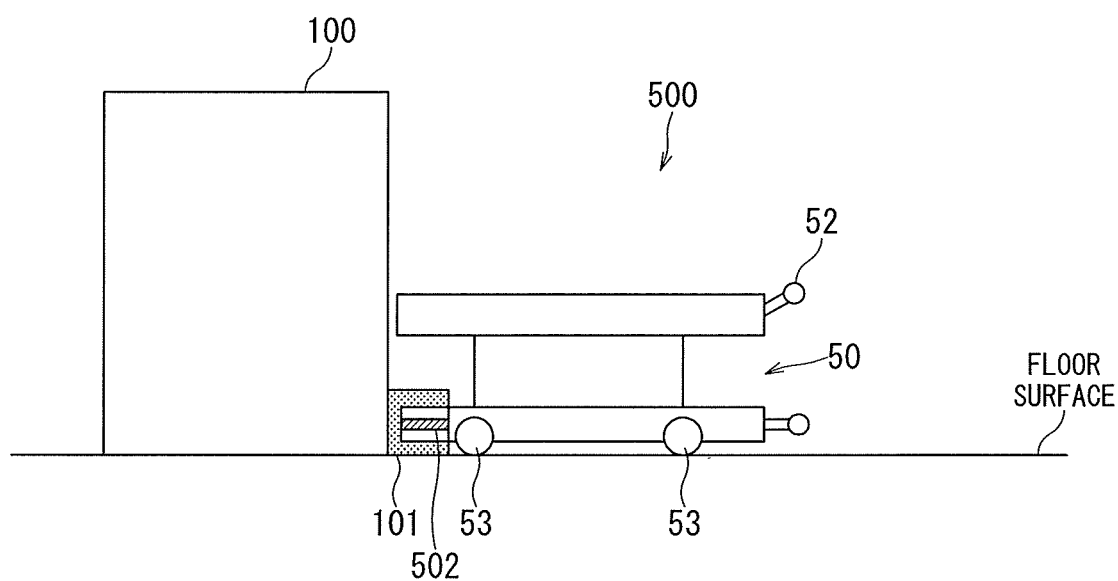
FIG. 2B is a schematic diagram illustrating a state where the bed system is mechanically connected to the main body.
Figure 3:
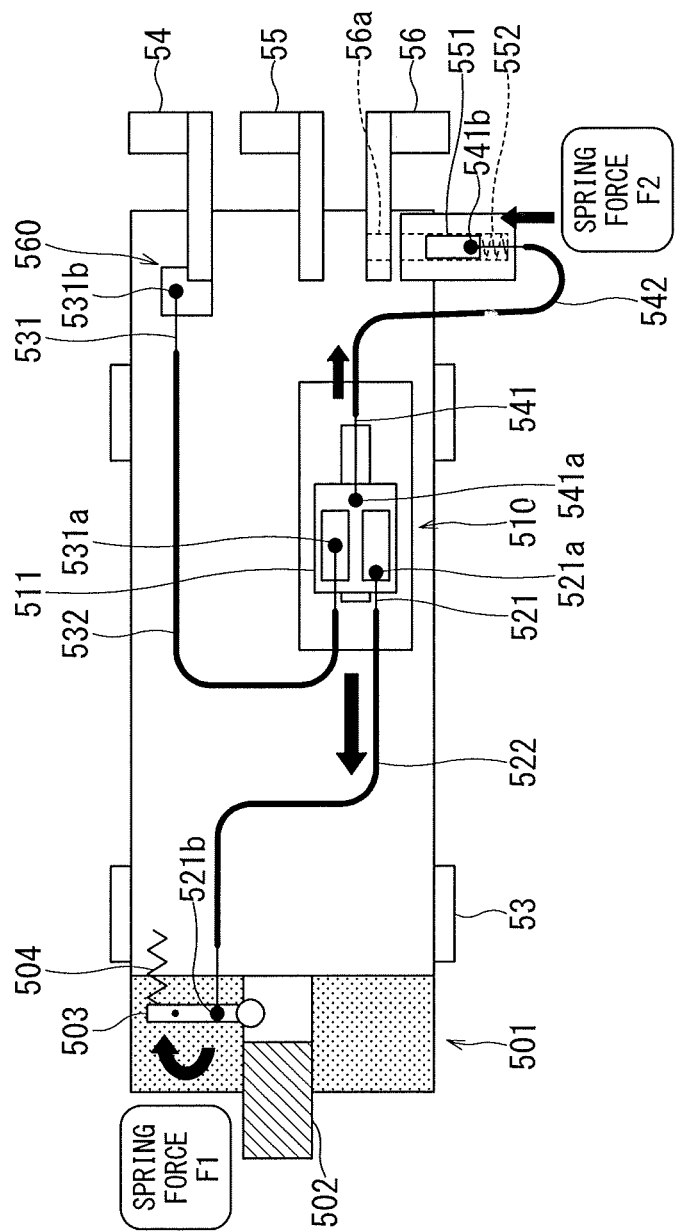
FIG. 3 is a schematic diagram illustrating an internal configuration of the bed system in the state where the bed system is mechanically separated from the main body.

FIG. 2A is a schematic diagram illustrating a state where the bed system 500 is mechanically separated from the main body 100. FIG. 2B is a schematic diagram illustrating a state where the bed system 500 is mechanically connected to the main body 100. FIG. 3 is a schematic diagram illustrating the internal configuration of the bed system 500 in the state where the bed system 500 is mechanically separated from the main body 100.

As shown in FIG. 2A and FIG. 2B, the bed system 500 according to the present embodiment is a so-called mobile device equipped with a handle 52, casters 53 provided between the bed system 500 and the floor surface. The casters 53 are one aspect of a traveling unit. Further, as shown in FIG. 3, the bed system 500 includes a caster lock pedal 54, a coupling pedal 55, and a separation pedal 56.

The bed system 500 according to the present embodiment controls the respective components such that permission of electrical connection with the main body 100 and lock of mechanical separation from the main body 100 are interlocked with an operation performed by a user at the time of mechanical connection and/or separation between the main body 100 and the bed system 500. The operation performed by a user at the time of mechanical connection and/or separation between the main body 100 and the bed system 500 includes an operation by which a predetermined member is brought into a predetermined state by the user and another operation by which the predetermined member is brought into a state different from the above-described predetermined state.

The operation performed by a user at the time of mechanical connection and/or separation between the main body 100 and the bed system 500 includes an operation to be performed after the mechanical connection and before imaging and another operation to be performed after imaging and before the mechanical separation. This type of operation includes operations of locking and unlocking the driving of the traveling unit. In addition, this type of operation includes an operation of lowering a side fence of the bed system 500, and an operation of moving the side fence to a position different from the lowered position (e.g., a raised position).

When the operation performed by a user at the time of mechanical connection and/or separation between the main body 100 and the bed system 500 is an operation of locking or unlocking the driving of the traveling unit, the predetermined member is a lock mechanism (e.g., stopper) of the traveling unit.

When the predetermined member is the lock mechanism, the above-described predetermined state is a state in which the lock mechanism of the traveling unit locks the traveling unit, and the above-described state different from the predetermined state is a state in which the lock mechanism of the traveling unit unlocks the traveling unit.

Further, when the above-described predetermined member is the lock mechanism, a user causes the state of the lock mechanism to transition via an interface configured to receive the operation of locking or unlocking the driving of the traveling unit.

FIG. 3 illustrates a case where the interface configured to receive the operation of locking or unlocking the driving of the casters 53 as one aspect of the traveling unit is the caster lock pedal 54.

The interface configured to receive the operation of locking or unlocking the driving of the traveling unit may be an input interface including at least one of a hard key and a soft key. The user can bring the state of the lock mechanism of the casters 53 into the state of locking the casters 53 or the state of unlocking the casters 53 by performing the operation of locking or unlocking the driving of the traveling unit via the hard key or the soft key of the input interface to which the instruction to lock the traveling unit and the instruction to unlock the traveling unit are assigned. In this case, the input interface may be provided at a position where the user can operate the bed system 500. Further, the input interface 43 of the console 400 may be used as the input interface.

When the operation performed by a user at the time of mechanical connection and/or separation between the main body 100 and the bed system 500 is an operation of moving the side fence of the bed system 500 to the lowered position or a position different from the lowered position (e.g., raised position), the above-described predetermined member is the side fence of the bed system 500.

When the predetermined member is the side fence of the bed system 500, the predetermined state is a state in which the side fence is fixed at the lowered position or is located at the lowered position. When the predetermined member is the side fence of the bed system 500, the state different from the predetermined state is a state in which the side fence is fixed at the position different from the lowered position (e.g., raised position) or is located at this position. The case of using the side fence will be described below by referring to FIG. 10.

First, a description will be given of a case where the predetermined member is the lock mechanism of the casters 53 and the interface configured to receive the operation of locking or unlocking the driving of the casters 53 is the caster lock pedal 54.

The bed system 500 includes a bed-side coupling unit 501 in addition to the caster lock pedal 54, the coupling pedal 55, and the separation pedal 56 as shown in FIG. 3. The bed-side coupling unit 501 includes a mechanical connection mechanism for mechanically connecting with a main-body-side coupling unit 101. In the following, a description will be given of a case where the mechanical connection mechanisms to be used are a fixing mechanism for mechanically and reliably connecting the main body 100 to the bed system 500 and connectors for connecting the wiring of the main body 100 to the wiring of the bed system 500.

In this case, when the bed system 500 is mechanically connected to the main body 100, first, it is preferable to mechanically and firmly connect the bed system 500 to the main body 100 by the fixing mechanism. Afterward, it is preferable to connect the wiring of the main body and the wiring of the bed system 500 to each other by mechanically connecting the respective connectors. By completing the connection with the use of the fixing mechanism, it is possible to accurately face the connectors each other, and thus it is possible to prevent an accident such as breakage of the connectors due to breakage of the pins of the connectors.

The locking mechanism is controlled by, e.g., a hydraulically operated cylinder. After the connection by the fixing mechanism is completed, the connectors are pushed in by the force of springs so as to be mechanically connected to each other.

In order to avoid a sudden short, electrical connection is not performed immediately after completion of both of the mechanical connection by the fixing mechanism and the connector connection, which includes mechanical connection by the connectors and the connection of the wirings by the connectors. At this time, a part of the wirings is in a state of being opened and thus energization from the main body 100 to the bed system 500 is impossible. Only when it is detected that the mechanical connection is completed and the electrical connection is permitted, the bed system 500 according to the present embodiment performs electrical connection with the main body 100.

The bed-side coupling unit 501 has a member for detecting a mechanical connection state by a mechanical connection mechanism. In the following, a description will be give of a case where an insertable piece 502 is used for a part of the member for detecting the mechanical connection state. The insertable piece 502 is configured to protrude from the bed-side coupling unit 501 when the bed system 500 is mechanically separated from the main body 100 (see FIG. 2A), and is also configured to be inserted into the bed-side coupling unit 501 when the bed system 500 is mechanically connected to the main body 100 (see FIG. 2B).

Various mechanical connecting mechanisms of this type are known in conventional technology, and any of these can be used. In the present embodiment, it is assumed that mechanical connection by the mechanical connection mechanism (hereinafter, arbitrarily referred to as mechanical connection) is reliably achieved by using the main-body-side coupling unit 101 and the bed-side coupling unit 501. In the present embodiment, a description will be given of a case where the mechanical connection is regarded to be completed when the insertable piece 502 is brought into the state of being pushed into the bed-side coupling unit 501.

The caster lock pedal 54 is a pedal capable of locking and unlocking the driving of the casters 53. When the bed system 500 is mechanically connected to the main body 100, the caster lock pedal 54 is manipulated by a user to lock the driving of the casters 53. The caster lock pedal 54 is one aspect of the interface configured to receive the operation of locking or unlocking the driving of the casters 53.

The coupling pedal 55 is a pedal for performing mechanical connection by the mechanical connecting mechanism. When the bed system 500 is mechanically and electrically separated from the main body 100, the coupling pedal 55 may function as either of a pedal for raising the table 51 and another pedal for lowering the table 51, for instance.

The separation pedal 56 is a pedal for mechanically separating the bed system 500 from the main body 100 when both are mechanically connected to each other. When the bed system 500 is mechanically and electrically separated from the main body 100, the separation pedal 56 may function as the other of the two pedals for raising and lowering the table 51 (i.e., may function as a pedal which is complementary to the coupling pedal 55), for instance.

When power supply to the devices in the energized state is unexpectedly and instantaneously shut off under the state where the bed system 500 is electrically connected to the main body 100, these devices are damaged in some cases. Thus, when the bed system 500 is mechanically and electrically connected to the main body 100, it is preferable that the electrical connection is not unintentionally separated.

For this reason, the bed system 500 according to the present embodiment includes a determiner 510 configured to determine permission of the mechanical separation. When the bed system 500 is mechanically and electrically connected to the main body 100, the determiner 510 determines that the mechanical separation is prohibited, and locks the mechanical separation operation by the separation pedal 56.

When the bed system 500 is mechanically connected to the main body 100 in the state where the electrical connection is permitted, the determiner 510 determines that the mechanical separation is prohibited. Further, when the bed system 500 is mechanically connected to main body 100 in the state where the electrical connection is prohibited, the determiner 510 determines that the mechanical separation is permitted.

Specifically, the operation on the separation pedal 56 is restricted depending on (a) the mechanical connection state between the main body 100 and the bed system 500 and (b) the electrical connection state as to whether the electrical connection between the main body 100 and the bed system 500 is permitted or prohibited. For instance, when the mechanical connection between the main body 100 and the bed system 500 is detected and it is detected that the electrical connection between the main body 100 and the bed system 500 is permitted, the separation pedal 56 is locked such that the operation for mechanically separating the bed system 500 from the main body 100 is prohibited.

As to whether the main body 100 and the bed system 500 are in the state of mechanically connected or separated, it can be determined on the basis of the state of the bed-side coupling unit 501 such as the insertable piece 502 as described above.

For instance, when the driving of the casters 53 is locked by the caster lock pedal 54, it can be expected that the user has an intention to fix the bed system 500 at the current position. Thus, when the driving of the casters 53 is locked under the state where the connectors are mechanically connected, the possibility that the user suddenly performs mechanical separation is considered to be low.

Thus, the bed system 500 according to the present embodiment interlocks the operation on the caster lock pedal 54 with the electrical connection. Specifically, when the casters 53 are locked by the caster lock pedal 54, the bed system 500 according to the present embodiment detects that the electrical connection is permitted. Further, when the driving of the casters 53 is unlocked by the caster lock pedal 54, it is detected that the electrical connection is prohibited and the bed system 500 is electrically separated from the main body 100.

Next, the configuration and operation of the bed system 500 according to the present embodiment will be described in detail.

As shown in FIG. 3, when the bed system 500 is mechanically connected to the main body 100 by the mechanical connection mechanism and the insertable piece 502 is pushed in, the insertable piece 502 deforms the spring 504 via the swing support piece 503.

As shown in FIG. 3, the bed system 500 includes, e.g., a coupling interlocking wire 521 equipped with an outer wire 522 as a transmission means for transmitting the movement amount of the insertable piece 502 to the block 511 of the determiner 510. As shown in FIG. 3, the bed system 500 includes, e.g., a caster pedal interlocking wire 531 equipped with an outer wire 532 as a transmission means for transmitting the operation amount of the caster lock pedal 54 to the block 511 of the determiner 510.

The block 511 of the determiner 510 moves according to the movement amount of the insertable piece 502 and the operation amount of the caster lock pedal 54, and operates as a so-called mechanical AND mechanism.

First, a description will be given of an operation example of the bed system 500 in the state where the bed system 500 is mechanically separated from the main body 100.

Figure 4:
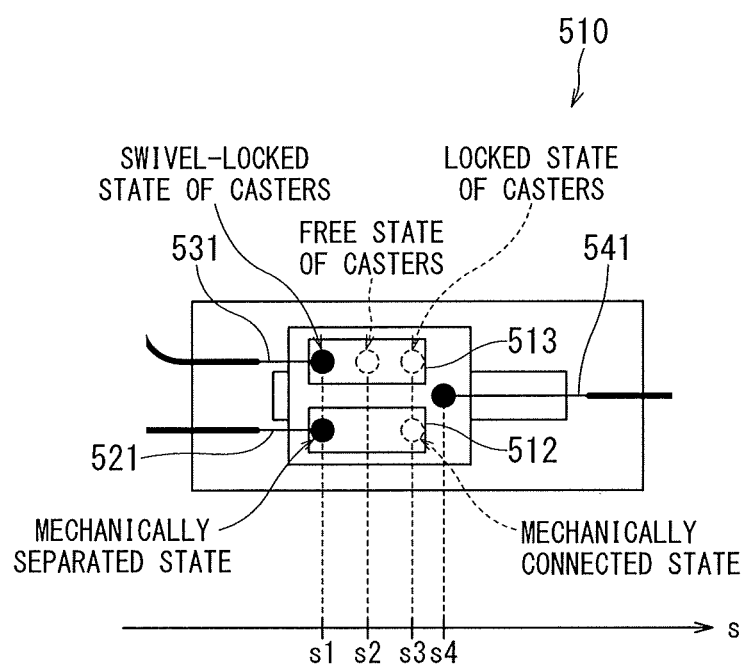
FIG. 4 is a schematic diagram illustrating an operation of a determiner in the state where the bed system is mechanically separated from the main body.

FIG. 4 is a schematic diagram illustrating one case of the operation of the determiner 510 in the state where the bed system 500 is mechanically separated from the main body 100.

Figure 5A:
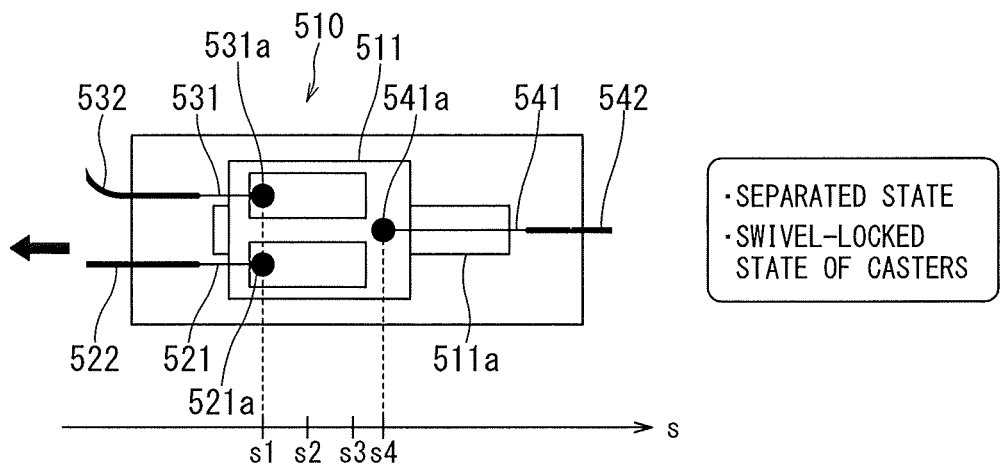
FIG. 5A is a schematic diagram illustrating an operation of the determiner in a state where the bed system is mechanically separated from the main body and the casters are in a swivel-locked state.
Figure 5B:
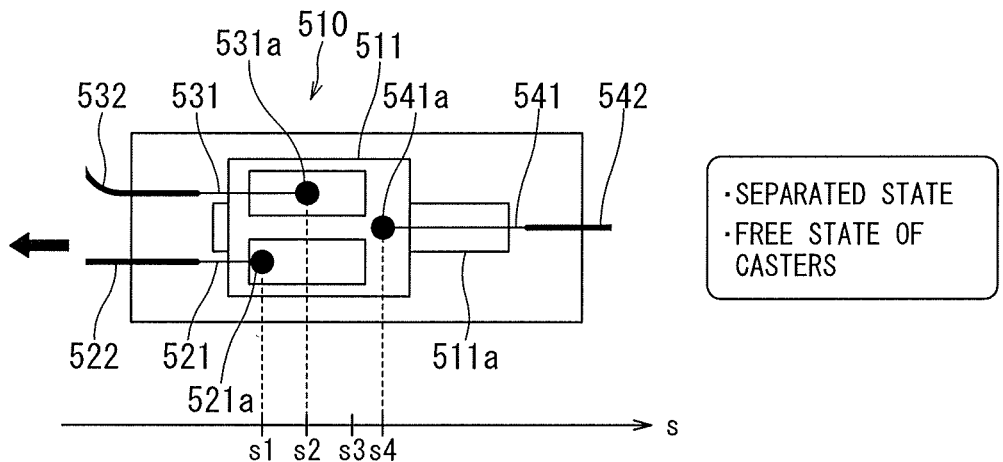
FIG. 5B is a schematic diagram illustrating an operation of the determiner in a state where the bed system is mechanically separated from the main body and the casters are in a free state.
Figure 5C:
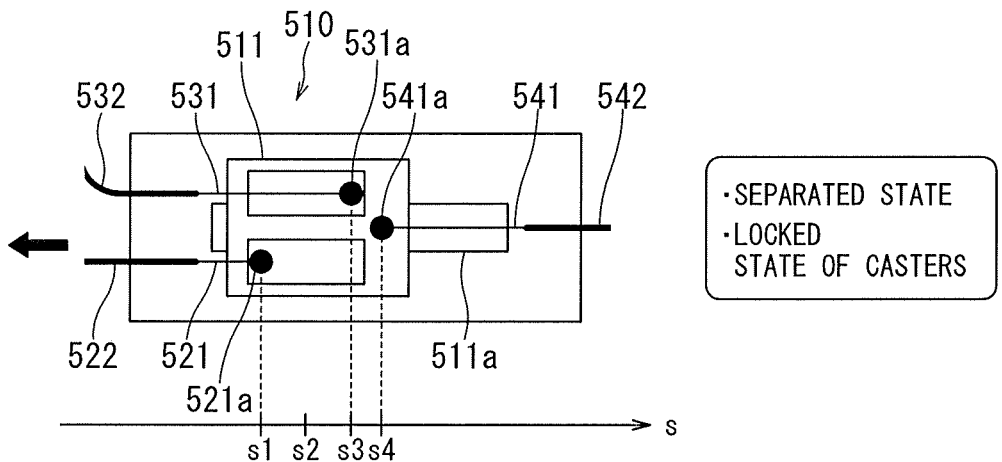
FIG. 5C is a schematic diagram illustrating an operation of the determiner in a state where the bed system is mechanically separated from the main body and the casters are in a completely locked state.

FIG. 5A to FIG. 5C are schematic diagrams illustrating operations of the determiner 510 in the state where the bed system is mechanically separated from the main body, FIG. 5A illustrates a case where the casters 53 are in a swivel-locked state, FIG. 5B illustrates a case where the casters 53 are in a free state, and FIG. 5C illustrates a case where the casters 53 are in a locked state.

The caster lock pedal 54 according to the present embodiment can switch the driving of the casters 53 to one of the three states including the swivel-locked state, the free state, and the locked state. In the swivel-locked state, straight-line movement of the casters 53 is allowed but the swivel (i.e., turning or change of progressing direction) of the casters 53 is prevented by, e.g., locking only the swivel of the right front wheel or the left front wheel. In the free state, the casters 53 are allowed to swivel in addition to that the casters 53 are allowed to perform the straight-line movement. In the locked state, the driving of the casters 53 is completely locked. Thus, in the swivel-locked state, it cannot be concluded that the user has an intention to fix the bed system 500 at the current position. In the present embodiment, the swivel-locked state is treated as the state in which the driving of the casters 53 is in the unlocked state similarly to the free state.

As shown in FIG. 3, the bed system 500 includes, e.g., a lock-pin interlocking wire 541 equipped with an outer wire 542 as a transmission means for transmitting the movement amount of the block 511.

The separation pedal 56 has an opening 56$a$ into which a separation lock pin 551 is inserted. The separation lock pin 551 is constantly biased toward the opening 56$a$ by a spring 552.

One end 521$a$ of the coupling interlocking wire 521 is positioned in the first restriction region 512 provided inside the block 511, and the other end 521$b$ of the coupling interlocking wire 521 is fixed to the swing support piece 503. One end 531$a$ of the caster pedal interlocking wire 531 is positioned in the second restriction region 513 provided inside the block 511, and the other end 531$b$ of the caster pedal interlocking wire 531 is connected to the caster-lock detection sensor 560 provided in the caster lock pedal 54. One end 541$a$ of the lock-pin interlocking wire 541 is fixed to the block 511, and the other end 541$b$ of the lock-pin interlocking wire 541 is fixed to the separation lock pin 551.

The caster-lock detection sensor 560 operates when the bed system 500 is mechanically connected to the main body 100, and outputs information indicating whether the casters 53 are in the locked state or unlocked state.

As shown in FIG. 3, the strength of the spring 504 of the bed-side coupling unit 501 and the strength of the spring 552 of the separation lock pin 551 are set such that the force F1 of pulling the coupling interlocking wire 521 by the spring 504 of the bed-side coupling unit 501 is stronger than the force F2 of pulling the lock-pin interlocking wire 541 by the spring 552 of the separation lock pin 551 in the state where the bed system 500 is mechanically separated from the main body 100.

Thus, in the state where the bed system 500 is mechanically separated from the main body 100, the one end 521$a$ of the coupling interlocking wire 521 positioned in the first restriction region 512 attracts the left side wall of the first restriction region 512 to the left side in the sheet of FIG. 4.

As shown in FIG. 5A to FIG. 5C, the moving direction of the block 511 along the rail 511$a$ is defined as "s". Further, when the block 511 is in motion along the rail 511$a$, the coordinate at which the one end 521$a$ of the coupling interlocking wire 521 is positioned is defined as s=s1. At this time, the one end 531$a$ of the caster pedal interlocking wire 531 positioned in the second restriction region 513 moves freely within the second restriction region 513 according to the operation on the caster lock pedal 54 as shown in FIG. 5A to FIG. 5C. In the following description, it is assumed that the one end 521$a$ is positioned at s=s1 in swivel-locked state, at s=s2 in the free state, and at s=s3 in the locked state.

As shown in FIG. 5A, FIG. 5B, and FIG. 5C, in the state where the bed system 500 is mechanically separated from the main body 100, the one end 541$a$ of the lock-pin interlocking wire 541 does not move from the position of s=s4 and the separation lock pin 551 is not inserted into the opening 56$a$ (see FIG. 3) of the separation pedal 56 regardless of the operation on the caster lock pedal 54.

Next, a description will be given of an operation example of the bed system 500 in the state where the bed system 500 is mechanically connected to the main body 100.

Figure 6:
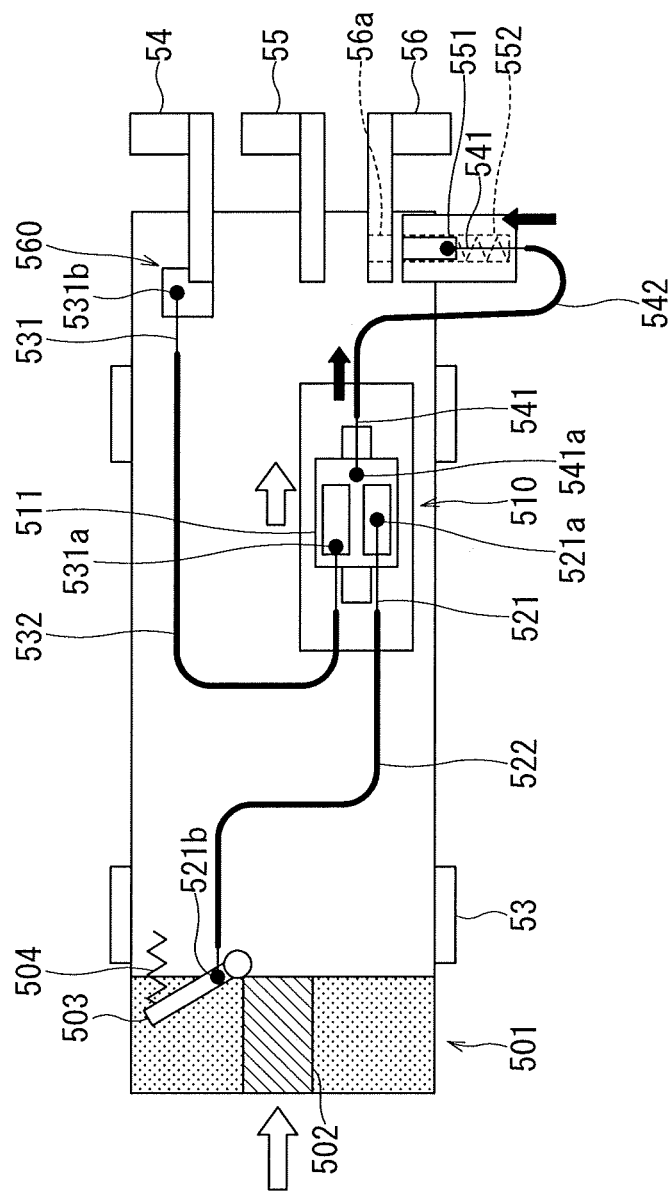
FIG. 6 is a schematic diagram illustrating the internal configuration of the bed system in a state where the bed system is mechanically connected to the main body and the casters are brought into the free state by a caster lock pedal.

FIG. 6 is a schematic diagram illustrating the internal configuration of the bed system 500 in the state where the bed system 500 is mechanically connected to the main body 100 and the casters 53 are brought into the free state by the caster lock pedal 54.

Figure 7:
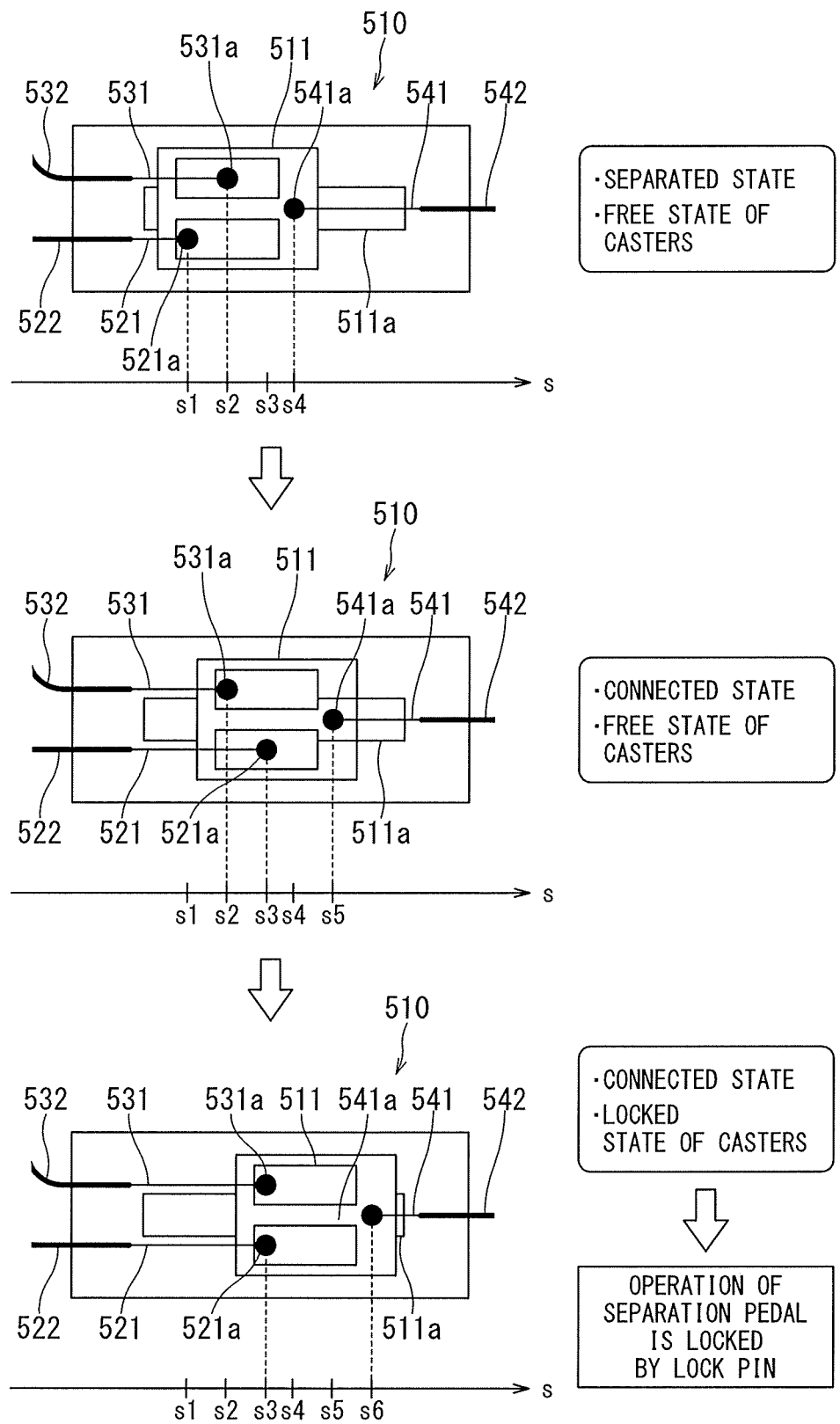
FIG. 7 is a schematic diagram illustrating state transition of the determiner from the state where the bed system is mechanically separated from the main body and the casters are in the free state (shown in the top part), to the state where the bed system is mechanically connected to the main body (shown in the middle part), and further to the completely locked state of the casters (shown in the bottom part)

FIG. 7 is a schematic diagram illustrating state transition of the determiner from the state where the bed system 500 is mechanically separated from the main body 100 and the casters 53 are in the free state (shown in the top part), to the state where both are mechanically connected (shown in the middle part), and further to the locked state (shown in the bottom part).

In the state where the bed system 500 is mechanically connected to the main body 100, the insertable piece 502 causes the biasing force of the spring 504 to be ineffective for the one end 521$a$ of the coupling interlocking wire 521, and this one end 521$a$ moves to the right side within the first restriction region 512 in the sheet of FIG. 6 according to the movement of the swing support piece 503. At this time, the one end 521$a$ is assumed to be positioned at s=s3 in the present embodiment (see FIG. 4).

Since the biasing force of the spring 504 becomes ineffective, the block 511 is attracted to the right side in the sheet of FIG. 6 by the biasing force of the spring 552 this time, and then the lock-pin interlocking wire 541 is sent out to the right side in the sheet of FIG. 6. At this time, the one end 531$a$ of the caster pedal interlocking wire 531 serves to stop the left side wall of the second restriction region 513. Thus, the position of the block 511 is defined according to the one end 531$a$ of the caster pedal interlocking wire 531, i.e., according to the operation on the caster lock pedal 54.

Accordingly, the separation lock pin 551 is designed to be inserted into the opening 56$a$ when the bed system 500 is mechanically connected to the main body 100 and the one end 541$a$ of the lock-pin interlocking wire 541 in the locked state is positioned at s=s6, and this design makes it possible to lock the separation operation by the separating pedal 56 when the bed system 500 is mechanically connected to the main body 100 in the locked state.

Figure 8:
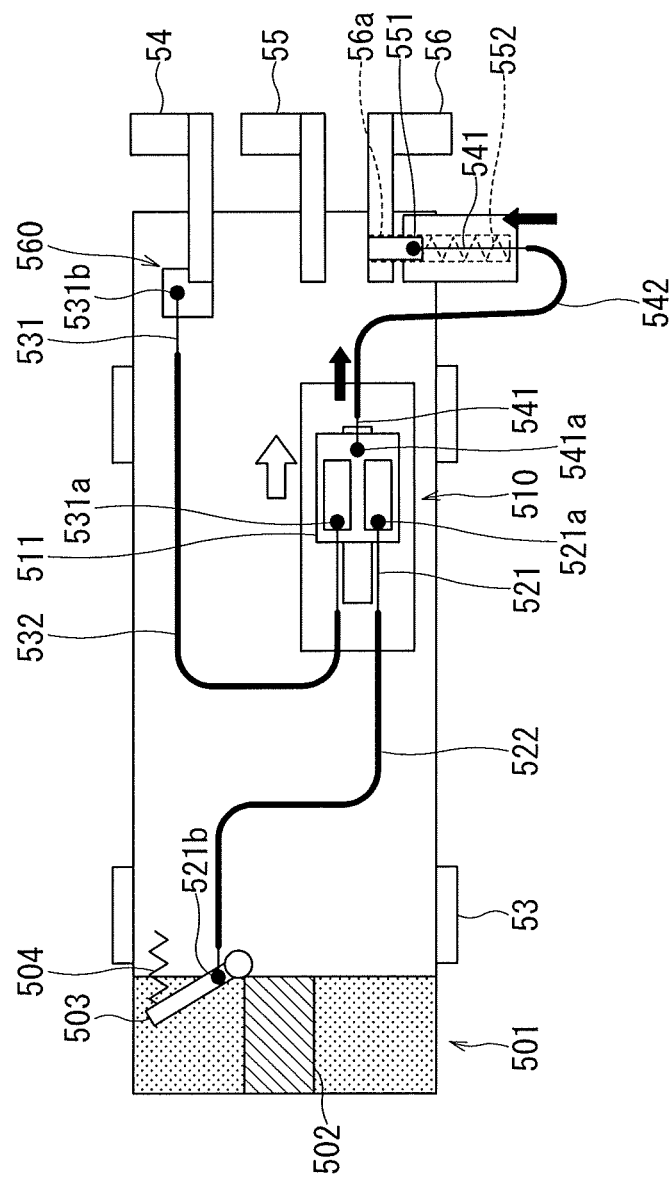
FIG. 8 is a schematic diagram illustrating the internal configuration of the bed system in a state where the bed system is mechanically connected to the main body and the casters are in the completely locked state by a caster lock pedal.

FIG. 8 is a schematic diagram illustrating the internal configuration of the bed system 500 in the state where the bed system 500 is mechanically connected to the main body 100 and the casters 53 are in the completely locked state by the caster lock pedal 54.

As shown in FIG. 8, when the bed system 500 is mechanically connected to the main body 100 and is in the locked state, the separation operation by the separation pedal 56 can be locked easily and reliably.

Next, a method for electrically connecting the bed system 500 to the main body 100 will be described.

Figure 9:
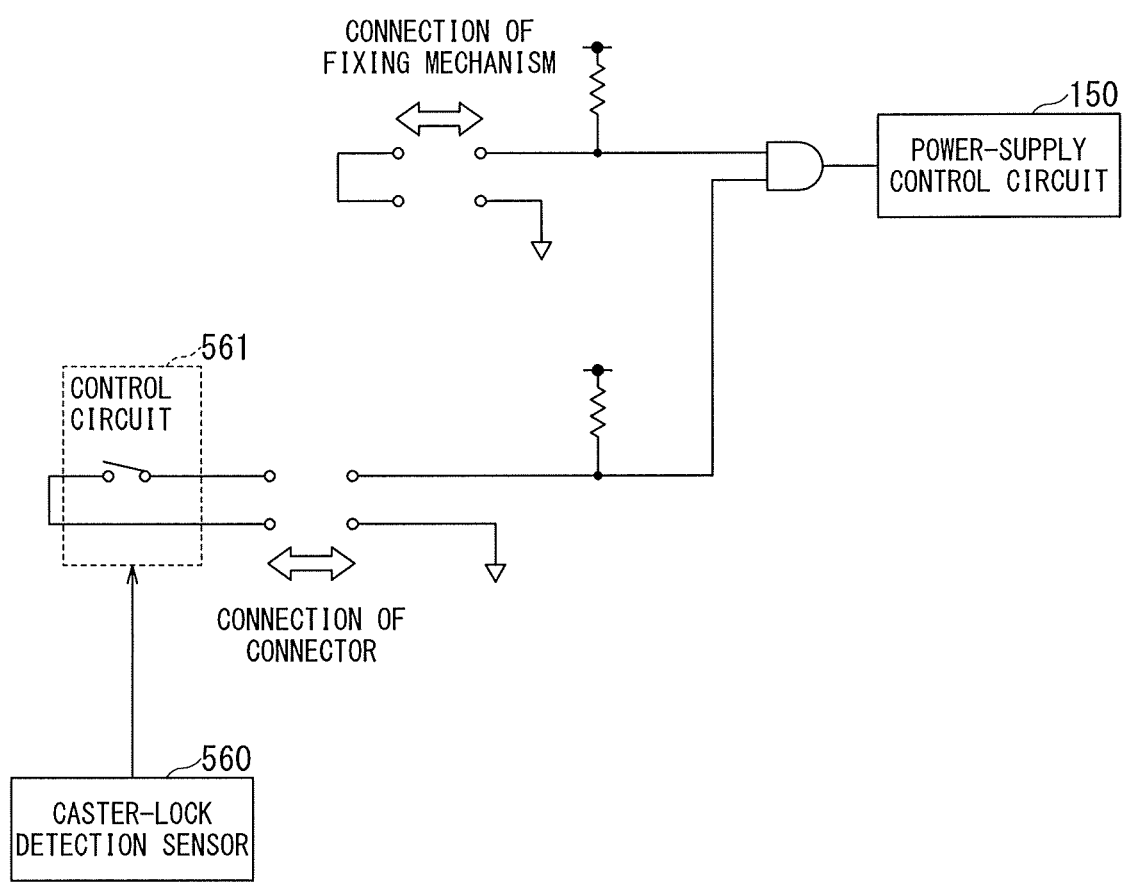
FIG. 9 is a schematic diagram illustrating a method of electrically connecting the bed system to the main body.

FIG. 9 is a schematic diagram illustrating a method of electrically connecting the bed system 500 to the main body 100.

As shown in FIG. 9, the main body 100 includes a power supply control circuit 150. An AND circuit is provided in the preceding stage of the power supply control circuit 150. A sensor output for detecting the mechanical connection by the fixing mechanism and another sensor output for detecting the mechanical connection by the connectors are inputted to the AND circuit.

The bed system 500 includes a control circuit 561. The control circuit 561 is configured as, e.g., a processor for executing predetermined programs or configured as hardware such as an FPGA or an ASIC. The control circuit 561 controls the electrical connection between the main body 100 and the bed system 500 and the electrical separation between both such that this control is interlocked with determination results of the determiner 510. For instance, when the control circuit 561 receives an output indicative of the locked state from the caster-lock detection sensor 560 in response to a user's operation with respect to the input interface or the caster lock pedal 54, the control circuit 561 may electrically connect the bed system 500 to the main body 100.

As described above, the caster-lock detection sensor 560 does not operate when the bed system 500 is not mechanically connected to the main body 100. Thus, when the control circuit 561 receives the output indicative of the locked state from the caster-lock detection sensor 560, the bed system 500 is mechanically connected to the main body 100. At the same time, the locked state is a state in which the electrical connection is permitted. Hence, when the control circuit 561 receives the output indicative of the locked state from the caster-lock detection sensor 560, the bed system 500 is mechanically connected to the main body 100 and both are in the state where the electrical connection is permitted, and thus the mechanical separation is prohibited.

When the control circuit 561 electrically connects the bed system 500 to the main body 100, the AND circuit outputs "1" and then the power supply control circuit 150 starts power supply to the bed system 500. At this time, in addition to the power supply, data transmission and data reception may be performed.

In the present embodiment, when the connectors are mechanically connected, a small current is supplied from the main body 100 to the caster-lock detection sensor 560 and the caster-lock detection sensor 560 starts operations. At this stage, however, the other components of the bed system 500 except the caster-lock detection sensor 560 are not supplied with electric power yet.

In the present embodiment, a description has been given of the case where each component of the bed system 500 does not use electric power but use, e.g., hydraulic pressure as a power source in the state where the bed system 500 is mechanically separated from the main body 100. However, the bed system 500 may be provided with a secondary battery. In this case, when the bed system 500 is mechanically and electrically connected to the main body 100, the power supply circuit of the main body 100 may be controlled by the power supply control circuit 150 so as to charge the secondary battery of the bed system 500.

The bed system 500 according to the present embodiment can perform the electrical connection with the main body 100 in conjunction with the operation performed at the time of the mechanical connection and separation between the main body 100 and the bed system 500 (i.e., can interlock both), similarly to the operation of the caster lock pedal 54. Additionally, when the bed system 500 is mechanically connected to the main body 100 and is in the state where the electrical connection is permitted (e.g., the driving of the casters 53 is in the locked state), the determiner 510 determines that the mechanical separation is prohibited and locks the mechanical separation operation by the separation pedal 56 as shown in the bottom part of FIG. 7. Further, when the determiner 510 determines that the electrical connection is prohibited (e.g., the driving of the casters 53 is in the unlocked state) as shown in the top part and the middle part of FIG. 7, the control circuit 561 electrically separates the bed system 500 from the main body 100.

Accordingly, it is possible to easily and reliably prevent an accident that the bed system 500 is unintentionally and mechanically separated from the main body 100 despite the electrically connected state between the main body 100 and the bed system 500. Thus, power supply to each device in the energized state is not unintentionally shut off momentarily. Hence, it is possible to prevent obstacles that may be caused by the above-described power supply interruption with respect to electrical components such as the operating mechanism of the motors of the bed system 500, the control board for sensor control and the power supply circuit of the main body 100.

When the bed system 500 is mechanically connected to the main body 100 and the separation operation by the separation pedal 56 can be locked in the locked state, instantaneous interruption of energization can be avoided. Thus, the bed system 500 may be configured such that the above-described swivel-locked state is excluded from the control of the bed system 500 and the driving of the caster 53 is unlocked only in the above-described free state. As another aspect, one or more states may be defined as the state in which the driving of the casters 53 is unlocked, in addition to the swivel-locked state and the free state.

Next, a description will be given of a case where the operation performed by the user at the time of the mechanical connection and/or separation between the main body 100 and the bed system 500 is the operation on a side fence 57 of the bed system 500.

Figure 10:
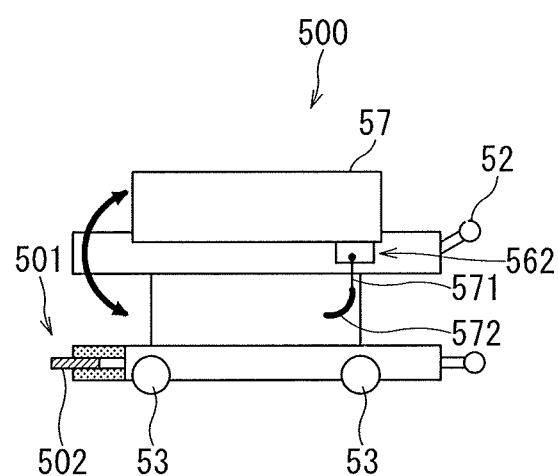
FIG. 10 is a schematic diagram illustrating a configuration of a bed system equipped with a side fence.

FIG. 10 is a schematic diagram illustrating a configuration of the bed system 500 equipped with the side fence 57. In the bed system 500, the side fence 57 may be provided in the vicinity of the position where an object is placed. The side fence 57 has, e.g., a flat plate shape. One side of the side fence 57 is swingably attached to the side surface of the bed body 50 or the table 51 via a hinge. The side fence 57 can be located at least at a raised position, a horizontally protruded position, and a lowered position. When the bed system 500 includes the side fence 57, it is considered that a user of the bed system 500 lowers the side fence 57 in the case of mechanically connecting the bed system 500 and the main body 100. Also when the bed system 500 includes the side fence 57, it is considered that the user raises the side fence 57 to prevent the object from falling during movement of the bed system 500 in the case of mechanically separating the bed system 500 from the main body.

Accordingly, instead of the state of the caster lock pedal 54 or together with the state of the caster lock pedal 54, the inclination of the side fence 57 may be used for determining whether the electrical connection between the main body 100 and the bed system 500 is permitted or prohibited.

FIG. 10 illustrates a case where the bed system 500 includes a fence interlocking wire 571 having an outer wire 572 as a transmission means for transmitting the operation amount of the side fence 57 to the block 511 and further includes a fence-state detection sensor 562 for outputting information on whether the side fence 57 is at the lowered position or not. As to the case where the side fence 57 is not lowered, this case includes a case where the side fence 57 rises vertically and another case where the side fence 57 protrudes horizontally as a table for placing the hand of the object during drip infusion or injection.

In this case, the bed system 500 interlocks the operation on the side fence 57 and the electrical connection. Specifically, when the side fence 57 is in the state of being located at the lowered position or is in the state of being positioned (fixed) in the lowered state, the bed system 500 detects that it is in the state where the electrical connection is permitted. Additionally, when the side fence 57 is in the state of being fixed at a position different from the lowered position (e.g., raised position) or is in the state of being located at this position, the bed system 500 detects that it is in the state where the electrical connection is prohibited and electrically separates the bed system 500 from the main body 100.

The fence interlocking wire 571 has the same configuration as the caster pedal interlocking wire 531, and one end of the fence interlocking wire 571 corresponds to one end 531*a* of the caster pedal interlocking wire 531. For example, under the state where the bed system 500 is mechanically connected to the main body 100, when the side fence 57 is located at the lowered position or positioned (fixed) in the lowered state, one end of the fence interlocking wire 571 is moved to the position s=s3 so as to lock the mechanical separation operation by the separation pedal 56 as shown in the bottom part of FIG. 7. Further, under the state where the bed system 500 is mechanically connected to the main body 100, when the side fence 57 is fixed or located at the position different from the lowered position, one end of the fence interlocking wire 571 is moved to the position s=s1 or s=s2 so as to unlock the mechanical separation operation by the separation pedal 56 as shown in the top or middle part of FIG. 7.

In other words, when the bed system 500 is mechanically connected to the main body 100 and the side fence 57 is at the lowered position (i.e., in the state where the electrical connection is permitted), the determiner 510 determines that the mechanical separation is prohibited and locks the mechanical separation operation by the separation pedal 56 as shown in the bottom part of FIG. 7. When the determiner 510 determines that the side fence 57 is at the position different from the lowered position (i.e., in the state where the electrical connection is prohibited) as shown in the top or middle part of FIG. 7, the control circuit 561 electrically separates the bed system 500 from the main body 100.

Figure 11:
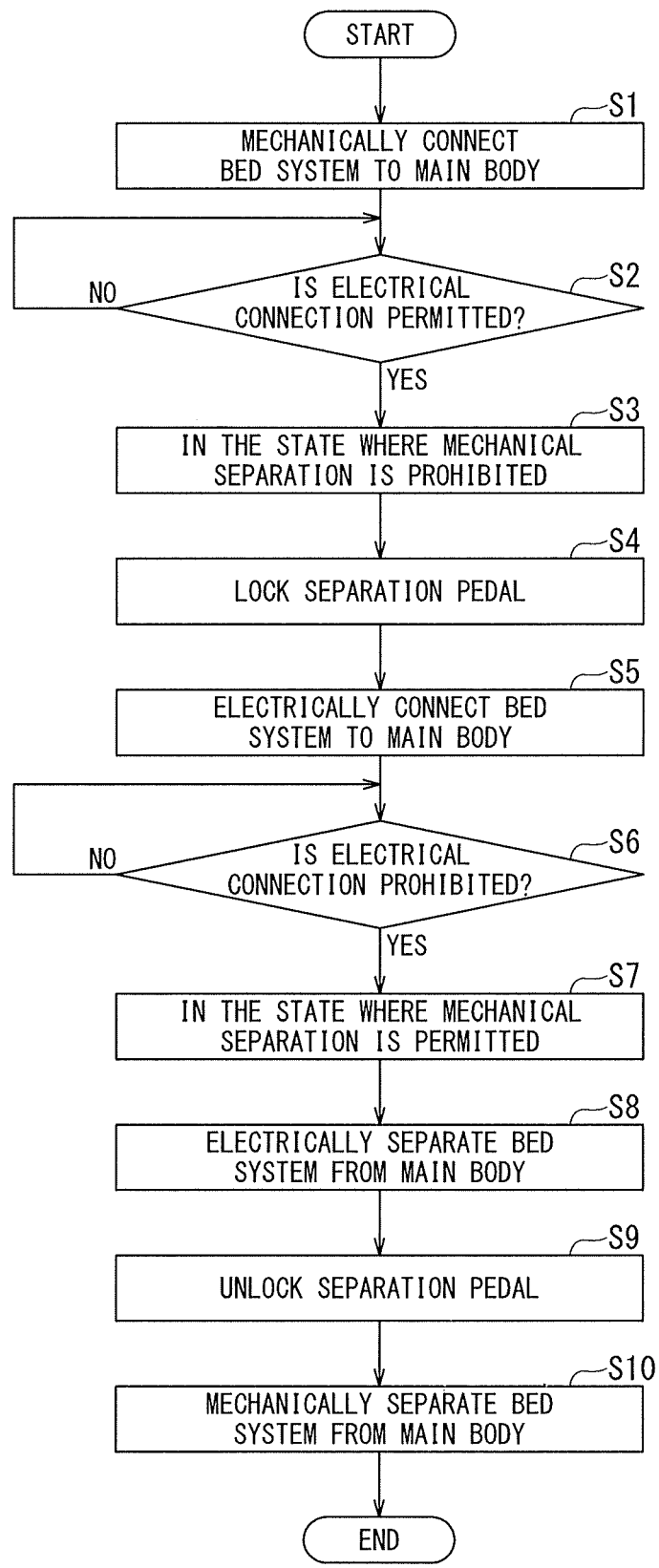
FIG. 11 is a flow chart illustrating a procedure for safely separating the bed system from the main body that is in the state of being connected to the bed system mechanically and electrically.

FIG. 11 is a flowchart focusing on a procedure for safely separating the bed system 500 from the main body 100 that is mechanically and electrically connected to the bed system 500. In FIG. 11, each reference sign composed of S and number on its right side indicates step number of the flowchart.

This procedure starts from the state where the bed system 500 is mechanically and electrically separated from the main body 100 (see FIG. 3 to FIG. 5).

First, in step S1, in preparation for imaging, the bed system 500 is moved near the main body 100 by a user, and then, the bed system 500 is mechanically connected to the main body 100.

In step S2, when the predetermined hardware member is brought into the predetermined state by the user in step S2, the determiner 510 detects that the electrical connection is permitted (corresponding to YES in FIG. 11), and then the processing proceeds to step S3. On the other hand, when the predetermined hardware is brought into the state different from the predetermined state by the user, the determiner 510 detects that the electrical connection is prohibited (corresponding to NO in FIG. 11), and continues the detection as to whether the electrical connection is permitted or prohibited In step S3, the determiner 510 determines that the mechanical separation is prohibited as shown in the bottom part of FIG. 7.

In step S4, it is in the state where the mechanical separation is prohibited, and one end 541*a* of the lock-pin interlocking wire 541 is located at s=s6 as shown in the bottom part of FIG. 7 so that the operation of the separation pedal 56 is locked. When the mechanical separation is prohibited as in steps S3 and S4, it is in the state where the electrical connection is permitted.

In step S5, the control circuit 561 electrically connects the bed system 500 to the main body 100 on the basis of the output indicative of the locked state from the caster-lock detection sensor 560 or the output from the fence-state detection sensor 562 indicating that the side fence 57 is at the lowered position.

In step S6, when the predetermined member maintains the predetermined state, the determiner 510 detects that the electrical connection is permitted (corresponding to NO in FIG. 11) and continues the detection as to whether the electrical connection is permitted or prohibited. In the step S6, when the predetermined member is brought into the state different from the predetermined state by the user, the determiner 510 detects that the electrical connection is prohibited (corresponding to YES in FIG. 11) and the processing proceeds to step S7.

In step S7, the determiner 510 determines that it is in the state where the mechanical separation is permitted as shown in the top or middle part of FIG. 7. When the mechanical separation is permitted as in step S7, it is in the state where the electrical connection is prohibited.

In step S8, the control circuit 561 electrically separates the bed system 500 from the main body 100 on the basis of the output indicative of the caster-unlocked state from the caster-lock detection sensor 560 or the output from the fence-state detection sensor 562 indicating that the side fence 57 is at the position different from the lowered position. Note that one end 541*a* of the lock-pin interlocking wire 541 is located at the position s=s4 or s=s5 as shown in the bottom part of FIG. 7 in the state where the mechanical separation is permitted.

In step S9, the operation of the separation pedal 56 is unlocked.

In step S10, the user mechanically separates the bed system 500 from the main body 100 by operating the separation pedal 56.

By the above-described procedure, it is possible to safely separate the bed system 500 from the main body 100 that is in the state of being mechanically and electrically connected to the bed system 500.

According to at least one embodiment described above, it is possible to safely separate a bed system from a main body of a medical image diagnosis apparatus that is in the state of being mechanically and electrically connected to the bed system.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A bed system that is mechanically and electrically connectable to a main body of a medical image diagnosis apparatus, the bed system comprising:
   a traveling unit provided between the bed system and a floor surface;
   an interface configured to receive an operation of locking or unlocking driving of the traveling unit,
   wherein, when the operation on the interface of locking or unlocking driving of the traveling unit is received in a state where the bed system is mechanically connected to the main body, an electrical connection is made between the bed system and the main body in conjunction with the operation.

2. The bed system according to claim 1, wherein when the driving of the traveling unit is locked according to an operation on the interface in the state where the bed system is mechanically connected to the main body, the bed system is electrically connected to the main body automatically in conjunction with the driving of the traveling unit being locked.

3. The bed system according to claim 1, wherein when the driving of the traveling unit is unlocked according to an operation on the interface in the state where the bed system is mechanically connected to the main body, the bed system is electrically separated from the main body automatically in conjunction with the driving of the traveling unit being unlocked.

4. The bed system according to claim 1, wherein the interface includes a lock pedal, the lock pedal capable of locking and unlocking the driving of the traveling unit.

5. The bed system according to claim 1, wherein the traveling unit includes a caster, and the interface receives the operation of locking or unlocking the driving of the caster.

6. The bed system according to claim 1, wherein the locking or unlocking of driving of the traveling unit is different from a mechanical connection or separation between the bed system and the main body.

7. The bed system according to claim 1, further comprising a control circuit configured to control the electrical connection.

8. The bed system according to claim 7, wherein, when the operation on the interface of locking or unlocking driving of the traveling unit is received in the state where the bed system is mechanically connected to the main body, the control circuit makes the electrical connection between the bed system and the main body in conjunction with the operation.

9. The bed system according to claim 1, wherein, when the operation on the interface of locking or unlocking driving of the traveling unit is received in the state where the bed system is mechanically connected to the main body, the electrical connection is automatically made between the bed system and the main body in conjunction with the operation.

* * * * *